(12) United States Patent
Kierce

(10) Patent No.: US 6,406,470 B1
(45) Date of Patent: Jun. 18, 2002

(54) SURGICAL PROBE AND VALUE ASSEMBLY AND THREADED QUICK DISCONNECT ADAPTER FOR USE THEREWITH

(75) Inventor: Paul C. Kierce, Hull, MA (US)

(73) Assignee: ATC Technologies, Inc., Woburn, MA (US)

( * ) Notice: Subject to any disclaimer, the term of this patent is extended or adjusted under 35 U.S.C. 154(b) by 0 days.

(21) Appl. No.: 09/507,854

(22) Filed: Feb. 22, 2000

(51) Int. Cl.$^7$ ............................................. A61M 25/16
(52) U.S. Cl. ........................ 604/535; 604/243; 604/905
(58) Field of Search ................................ 604/533–535, 604/30, 27, 243, 246, 905, 248, 249, 240, 241

(56) References Cited

U.S. PATENT DOCUMENTS

| | | |
|---|---|---|
| 738,503 A | 9/1903 | Waters |
| 1,538,007 A | 5/1925 | Schellin |
| 2,902,995 A | 9/1959 | Loper |
| 3,245,703 A | 4/1966 | Manly |
| 3,484,121 A | 12/1969 | Quinton |
| 3,707,972 A | 1/1973 | Villari et al. |
| 3,887,222 A | 6/1975 | Hammond |
| 3,921,297 A | 11/1975 | Vit |
| 4,080,737 A | 3/1978 | Fleer |
| 4,123,091 A | 10/1978 | Cosentino et al. |
| 4,149,315 A | 4/1979 | Page, Jr, et al. |
| 4,248,589 A | 2/1981 | Lewis |
| 4,257,416 A | 3/1981 | Prager |
| 4,266,815 A | 5/1981 | Cross |
| 4,310,185 A | 1/1982 | Bartholomew |
| 4,430,080 A | 2/1984 | Pasquini et al. |
| 4,451,069 A | 5/1984 | Melone |
| 4,451,257 A | 5/1984 | Atchley |
| 4,484,769 A | 11/1984 | Lacey |
| 4,580,816 A | 4/1986 | Campbell et al. |
| 4,592,749 A | 6/1986 | Ebling et al. |
| 4,612,929 A | 9/1986 | Schubert et al. |
| 4,619,640 A | 10/1986 | Potolsky et al. |
| 4,660,803 A | 4/1987 | Johnston et al. |
| 4,673,200 A | 6/1987 | Miyauchi |
| 4,863,202 A | 9/1989 | Oldford |
| 4,872,837 A | 10/1989 | Issalene et al. |
| 4,878,900 A | 11/1989 | Sundt |
| 4,925,450 A | 5/1990 | Imonti et al. |
| 4,942,873 A | 7/1990 | Irwin et al. |
| 4,946,204 A | 8/1990 | Boticki |
| 4,951,977 A | 8/1990 | Shutt |
| 5,039,304 A | 8/1991 | Heil |

(List continued on next page.)

FOREIGN PATENT DOCUMENTS

| | | |
|---|---|---|
| DE | 2905035 | 8/1979 |
| WO | WO 9317733 | 9/1993 |

Primary Examiner—Brian L. Casler
Assistant Examiner—Jeremy Thissell
(74) Attorney, Agent, or Firm—Devine, Millimet & Branch, PA; Kevin J. Carroll; Paul C. Remus

(57) ABSTRACT

A threaded quick disconnect adapter is used to connect one or more different surgical probes, such as laparoscopic probes, to a valve device, such as a trumpet valve. The threaded quick disconnect adapter includes an adapter body having first and second ends. A valve engaging portion is disposed on the first end of the adapter body and is preferably threaded to threadably engaging an outlet on the valve. A threaded probe engaging portion is disposed on the second end of the adapter body for threadably engaging a probe base on one of the probes. A sealing portion, such as an O-ring, is also disposed on the second end for sealing with the probe base. The threaded probe engaging portion has a larger outer diameter than the sealing portion. In one example, the probe is attached with first a linear motion to engage the probe base with the sealing portion and then a rotating or twisting motion to thread the probe base on the threaded probe engaging portion.

24 Claims, 3 Drawing Sheets

U.S. PATENT DOCUMENTS

| | | |
|---|---|---|
| 5,049,017 A | 9/1991 | Reynolds |
| 5,049,071 A | 9/1991 | Davis et al. |
| 5,057,015 A | 10/1991 | Fleer |
| 5,078,433 A | 1/1992 | Morse et al. |
| 5,161,542 A * | 11/1992 | Palestrant .................... 600/567 |
| 5,188,591 A | 2/1993 | Dorsey, III ................... 604/33 |
| 5,275,612 A | 1/1994 | Bales, Jr. |
| 5,330,235 A | 7/1994 | Wagner et al. |
| 5,509,911 A | 4/1996 | Cottone, Sr. et al. |
| 5,549,583 A | 8/1996 | Sanford et al. |
| 5,653,591 A | 8/1997 | Loge |
| 5,655,906 A | 8/1997 | Coss et al. |
| 5,713,573 A * | 2/1998 | Jehle |
| 5,868,773 A * | 2/1999 | Danks et al. |
| 6,095,572 A * | 8/2000 | Ford et al. |
| 6,206,510 B1 * | 3/2001 | Casserino et al. |

* cited by examiner

SURGICAL PROBE AND VALUE ASSEMBLY AND THREADED QUICK DISCONNECT ADAPTER FOR USE THEREWITH

FIELD OF THE INVENTION

The present invention relates to medical instruments and more particularly, a surgical probe and valve assembly and threaded quick disconnect adapter used to connect a valve device to probes used in laparoscopic surgery.

BACKGROUND OF THE INVENTION

Laparoscopy has become increasingly popular as a less invasive procedure than traditional surgical procedures. Laparoscopy is commonly known as a surgical procedure in which a scope is inserted into the abdomen of a patient through a small incision. One type of medical device commonly used in laparoscopy is a suction/irrigator, which is capable of providing both suction and irrigation at the desired location within the patient. A suction/irrigator typically includes a valve device for controlling the suction/irrigation and a cannula or probe extending from the valve device. One example of the valve device is commonly known as a trumpet valve and is disclosed in greater detail in U.S. Pat. No. 5,188,591, incorporated herein by reference. Different types of probes have been designed for different types of procedures or functions.

In use, the probe attached to the valve device is inserted into the incision within the patient to perform a surgical operation while enabling suction and irrigation of fluids within the patient. During electrosurgical laparoscopy, the suction might also be used to evacuate smoke created as a byproduct of the electrosurgery. Sometimes, during a procedure, probes having different tip designs are needed for different functions. At one time, suction/irrigators were made with the probe permanently fixed to the valve as a one piece unit. Thus, if a physician needed to change the type of probe during a procedure, the entire unit needed to be replaced.

As a result of this inconvenience, interchangeable, detachable probes were developed, that can be attached to and detached from the trumpet valve during a procedure. Initially, a threaded connection was used between the probes and valve device. Because threading and unthreading the probes using these earlier threaded connections required too much time during the surgical procedure, quick disconnect fittings were designed in an effort to provide faster attachment and detachment. One example of such a quick disconnect fitting is disclosed in greater detail in U.S. Pat. No. 5,803,510, incorporated herein by reference. This type of quick disconnect fitting uses a detent/groove combination that provides for quick attachment and detachment of a probe tip to the fitting without having to thread the probe onto the fitting.

Although this quick disconnect fitting enables a quicker attachment and detachment of probes, this fitting is susceptible to the accidental detachment of the probe since only friction holds the probe onto the adapter. When surgeons use the probe to lift or move organs, this pressure on the probe may cause detachment as well as stress on the adapter. If the adapter wall is too thin to hold up under such stress, the adapter may break off the trumpet valve, for example, when the probe is used as a retractor. Reliance on a friction fit for engagement between the probe and adapter may also result in a connection that is either too loose or too tight, particularly when the adapter is made of plastic and the probe hub is made of metal. Repeated use by way of the push/pull attachment also causes wear, resulting in a loose fitting that is even more susceptible to inadvertent detachment.

Accordingly, a need exists for a threaded quick disconnect adapter that provides a quicker attachment and detachment than the conventional threaded connection while assuring that the probe cannot accidentally be detached merely by pulling the probe and/or valve in a linear direction.

SUMMARY OF THE INVENTION

The present invention features a threaded quick disconnect adapter for connecting probes to a valve device. The adapter comprises an adapter body having a first end and a second end and defining an inner passageway extending from the first end to the second end. A valve engaging portion is disposed on the first end of the adapter body for engaging the valve device. A threaded probe engaging portion is disposed on a second end of the adapter body for engaging a probe base on one of the probes. A sealing portion is also disposed on the second end of the adapter body for sealing against the probe base.

The valve engaging portion is preferably threaded to threadably engage a corresponding threaded region on the probe fitting on the valve device. The threaded probe engaging portion preferably has an outer diameter greater than an outer diameter of the sealing portion. The sealing portion preferably includes one or more annular grooves disposed around the second end of the adapter body and one or more O-rings seated within the respective one or more annular grooves. In one embodiment, a collar is disposed between the valve engaging portion and the probe engaging portion.

The present invention also features a surgical assembly including any combination of the threaded quick disconnect adapter, the valve device, and one or more probes.

The present invention also features a valve having the adapter integrally attached or as one-piece with the valve outlet.

BRIEF DESCRIPTION OF THE DRAWINGS

These and other features and advantages of the present invention will be better understood by reading the following detailed description, taken together with the drawings wherein.

DETAILED DESCRIPTION OF THE PREFERRED EMBODIMENT

Figure 1:
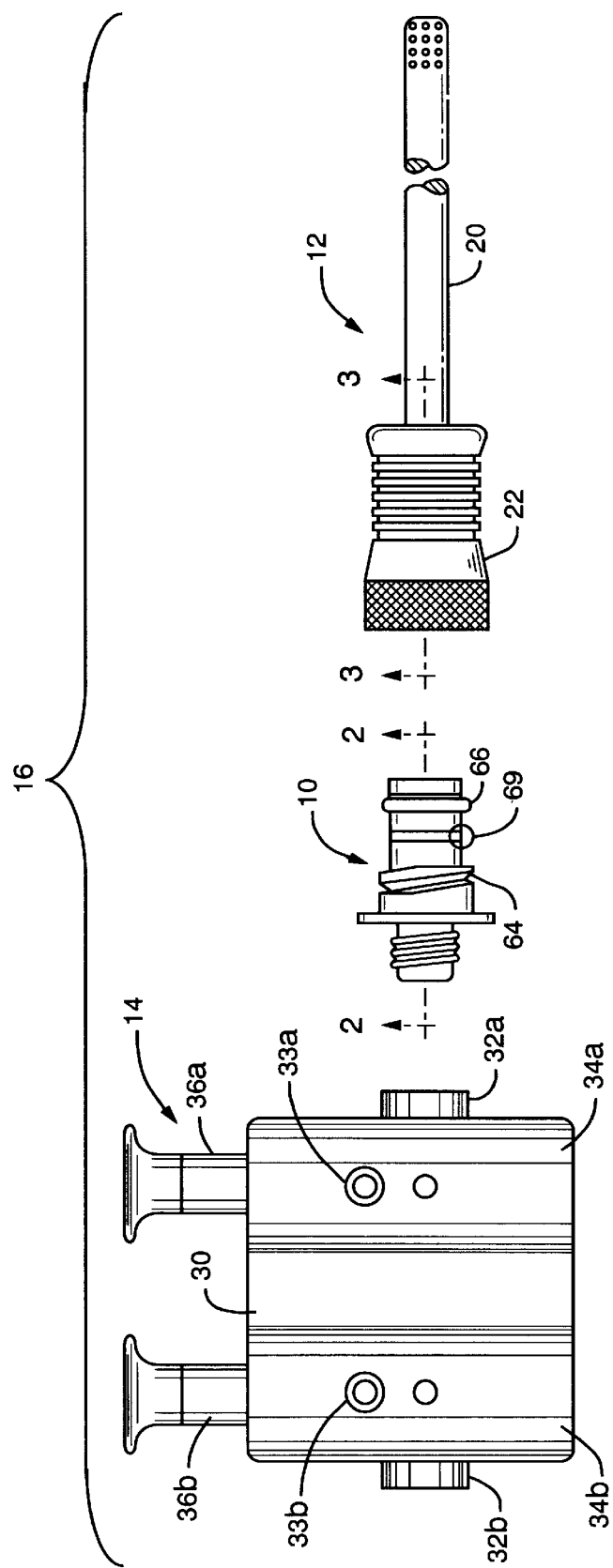
FIG. 1 is an exploded view of a surgical valve and probe assembly including a threaded quick disconnect adapter, according to one embodiment of the present invention.

The threaded quick disconnect adapter 10, FIG. 1, is preferably used to connect different types of probes 12 to a valve device 14. Although the exemplary embodiment shown and described below includes a trumpet valve and an electrosurgical probe, the threaded quick disconnect adapter 10 of the present invention can be used to connect any type of probe to any type of valve device, aspirator, or other device capable of providing suction and/or irrigation. The assembly 16 including the threaded quick disconnect adapter 10, the probe 12, and the valve device 14 is preferably used in laparoscopy for suction/irrigation but could also be used for other purposes in other types of medical or dental procedures.

The probe 12 includes a probe tip 20 and a probe base 22. The valve device 14 includes a valve body 30 having at least one outlet or fitting 32. In the exemplary embodiment, the valve device 14 is a trumpet valve having a pair of probe fittings 32a, 32b and a pair of source fittings 33a, 33b communicating with respective valve chambers 34a, 34b. The probe fittings 32a, 32b can be connected to probes 12 and the source fittings 32a, 32b can be connected to a source of vacuum and/or irrigation fluid. A pair of reciprocating pistons 36a, 36b within the respective valve chambers 34a, 34b control the suction/irrigation through the valve chambers 34a, 34b. This type of trumpet valve is described further in U.S. Pat. No. 5,188,591, incorporated herein by reference.

Figure 2:
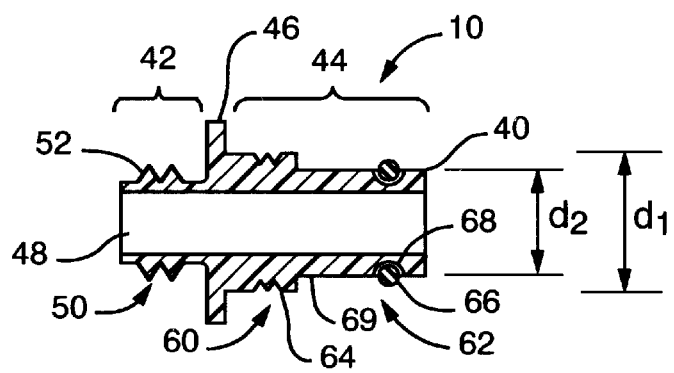
FIG. 2 is a cross-sectional view of the threaded quick disconnect adapter, according to one embodiment of the present invention.

The threaded quick disconnect adapter 10, FIG. 2, includes an adapter body 40 having a first end 42, a second end 44, and a collar 46 separating the first end 42 from the second end 44. The adapter body 40 defines an inner passageway 48 extending through first end 42 and second end 44. In one example, the adapter body 40 is made of a plastic material, such as the type known as DELRIN®. The probe base 22 is preferably made of a material similar to the material of the adapter body 40, such as DELRIN® or another plastic material. Alternatively, the probe base 22 can be made of other materials, such as aluminum.

Figure 3:
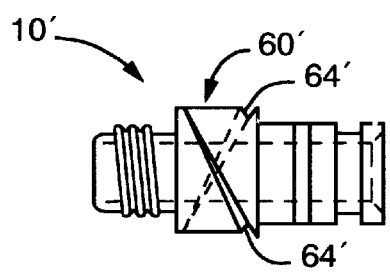
FIG. 3 is an elevational view of the threaded quick disconnect adapter, according to another embodiment of the present invention.

Although the collar 46 is shown as having a generally circular shape, other shapes and configurations are contemplated. For example, the collar 46 can have a sleeve-like configuration such that the collar 46 extends over the probe fittings 32a, 32b (not shown). Another embodiment of the adapter 10', FIG. 3, does not include the collar 46.

The threaded quick disconnect adapter 10 includes a valve engaging portion 50 at the first end 42 of the adapter body 40. The valve engaging portion 50 engages with one of the probe fittings 32a, 32b on the valve device 14 (FIG. 1). In the exemplary embodiment, the valve engaging portion 50 includes external threads 52 that mate with internal threads within the probe fittings 32a, 32b. The valve engaging portion 50 can also include other types of engagements to engage with the probe fittings 32a, 32b. Although the exemplary embodiment shows the valve engaging portion as the male and the probe fittings 32a, 32b as the female, this can be reversed. An O-ring can be positioned on the valve engaging portion 50 for sealing against the probe fitting 32a of the valve device 14.

The threaded quick disconnect adapter 10 also includes a threaded probe engaging portion 60 and a sealing portion 62 on the second end 44 of the adapter body 40. The outer diameter $d_1$ of the threaded probe engaging portion 60 is preferably greater than the outer diameter $d_2$ of the sealing portion 62 to provide a thicker wall for machining the thread grooves or "pitch diameters" of the threads, as described below. Providing a thicker wall also strengthens the adapter 10 to prevent the adapter 10 from breaking off when under stress during use.

In the embodiment of the adapter 10' without the collar 46 (FIG. 3), the outside diameter $d_1$ of the threaded probe engaging portion 60' is comparable to the outside diameter of the outlet or fitting 32a of the valve device 14. This allows probe base 22 to engage onto the threaded probe engaging portion 60', past the adapter 10' and over the outlet or fitting 32a of the valve device 14, thereby providing added support if the user needs additional leverage strength. The adapter body 40 is also designed for stability and conformity to standard trumpet valves, aspirators, or other similar devices such that the valve or other device having the adapter can be easily held in the palm of a left handed or right handed surgeon.

Figure 4:
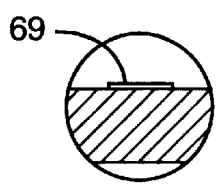
FIG. 4 is a cross-sectional view of the raised annular region on the adapter, according to one embodiment of the present invention.

The sealing portion 62 preferably includes sealing member 66, such as an O-ring disposed within a groove 68 in the sealing portion 62, for sealing against an inner surface of the probe base 22 on the probe 12. The sealing portion 62 also includes a raised annular portion 69, FIG. 4, extending around the adapter body 40 to provide a tactile indication to the user when the probe base 22 moves over the raised annular portion 69 on the adapter 10. As an alternative to the raised annular portion 69, the adapter 10 can include a snap ring (not shown) seated in a groove around the adapter body 40.

Figure 5:
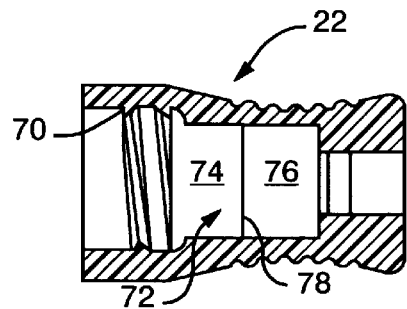
FIG. 5 is a cross-sectional view of a probe base on the probe, according to one embodiment of the present invention.
Figure 6:
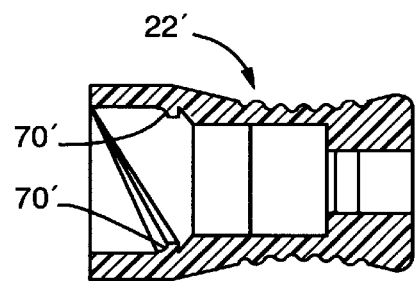
FIG. 6 is a cross-sectional view of a probe base on the probe, according to another embodiment of the present invention.

In the exemplary embodiment, the probe base 22, FIG. 5, of the probe 12 has an internal thread 70 that engages the external thread 64 of the threaded probe engaging portion 60. The external and internal threads 64, 70 generally comply with international thread standards with some custom design modifications to provide a quicker turn. The major and minor diameters are preferably constructed to fit consistently while allowing the internal thread 70 to pass over the raised surface 69 (or snap ring) and o-ring 66 on the adapter 10. The threads 70, 64 preferably have a maximum of 2 threads per inch requiring less than a ¼ turn to fully engage the threads. In the preferred embodiment, the threads have a double start lead as shown, for example, on the adapter 10' and probe base 22' (FIGS. 3 and 6), which allows the threads to be more quickly engaged with less rotation.

The probe base 22 further includes an inner sealing portion 72 having a first region 74, a second region 76 with a slightly smaller inner diameter than the first region 74, and a chamfer 78 between the first and second regions 74, 76. When the probe base 22 is engaged with the adapter 10, the O-ring 66 passes through the first region 74 and is seated against the second region 76 having the slightly smaller inner diameter to effect the seal.

In use, the threaded quick disconnect adapter 10 is attached to the valve device 14, for example, by threading the valve engaging portion 50 into the port fitting 32a. The probe 20 is then engaged with the threaded quick disconnect adapter 10 first by sliding the probe base 22 over the sealing portion 62 using a linear motion and then by threading the probe base 22 onto the threaded probe engaging portion 62 using a turning motion. The engagement of the raised annular portion 69 with the inner sealing portion 72 of the probe base 22 provides a tactile indication or "click" feature that allows the user to quickly thread on the probe 12 to the adapter 10 and feel it engage, signaling that the probe is fully engaged and sealed to the adapter.

Because the probe 20 of the present invention must be rotated to detach from the adapter 10, the probe 20 cannot be accidentally detached by pulling in a linear direction. The raised annular portion 69 also provides some assurance against disconnection if the valve or probe is accidentally twisted and unthreaded. This present invention thus provides both a quick and secure connection between the threaded probe base 22 on the probe 20 and the threaded quick disconnect adapter 10. The threaded probe engaging portion 60 may be capable of engaging with other non-threaded probe bases by way of a friction fit. Although this type of connection will not be as secure as the threaded engagement, this feature makes the threaded quick disconnect adapter of the present invention more versatile.

Figure 7:
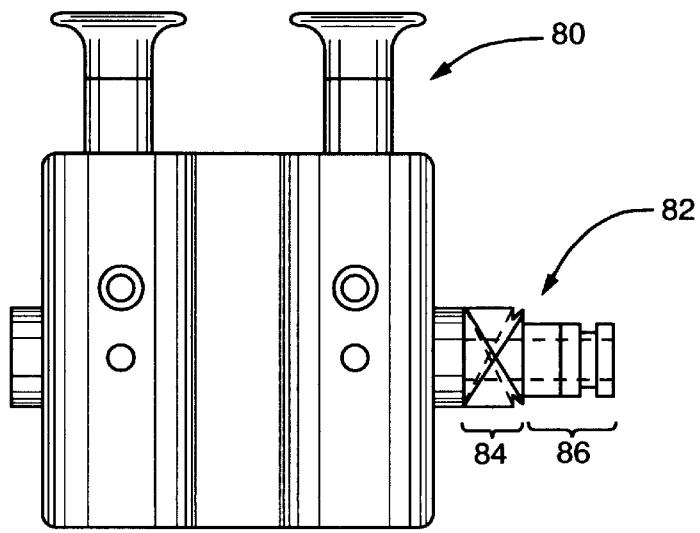
FIG. 7 is an elevational view of an adapter integrally attached or one-piece with a valve device, according to another embodiment of the present invention.

According to an alternative embodiment, a valve device 80, FIG. 7, includes a threaded quick disconnect probe fitting 82 formed integrally with (e.g., permanently bonded) or as one-piece (e.g., molded together) with the valve device 80. The threaded quick disconnect probe fitting 82 has a threaded probe engaging portion 84 and a sealing portion 86 similar to the adapter described above.

Accordingly, the threaded quick disconnect adapter of the present invention provides a more secure engagement than conventional push/pull type quick disconnect adapters while also allowing a quicker attachment and detachment than conventional threading.

Modifications and substitutions by one of ordinary skill in the art are considered to be within the scope of the present invention, which is not to be limited except by the following claims.

What is claimed is:

1. A threaded quick disconnect adapter for connecting surgical probes to a valve device, said adapter comprising:
    an adapter body having a first end and a second end, said adapter body defining an inner passageway extending from said first end to said second end;
    a valve engaging portion disposed on said first end of said adapter body for engaging a probe fitting of the valve device;
    a threaded probe engaging portion disposed on said second end of said adapter body for engaging a probe base on one of said probes, wherein said threaded probe engaging portion includes a thread providing less than about ¼ turn to fully engage with said probe base; and
    a sealing portion disposed on said second end of said adapter body, said sealing portion including at least one annular sealing member raised above a surface of said second end of said adapter body for sealing against said probe base of said probe, wherein said threaded probe engaging portion is located between said sealing portion and said valve engaging portion.

2. The threaded quick disconnect adapter of claim 1 wherein said valve engaging portion is threaded for engaging a threaded region on said probe fitting on said valve device.

3. The threaded quick disconnect adapter of claim 1 wherein said valve engaging portion includes an O-ring for sealing against said probe fitting of said valve device.

4. The threaded quick disconnect adapter of claim 1 wherein said threaded probe engaging portion has an outer diameter greater than an outer diameter of said sealing portion.

5. The threaded quick disconnect adapter of claim 1 wherein said thread has a double start lead.

6. The threaded quick disconnect adapter of claim 1 wherein said sealing portion includes at least one annular groove disposed around said second end of said adapter body, and wherein said sealing member includes at least one O-ring seated within said at least one annular groove.

7. The threaded quick disconnect adapter of claim 6 wherein said sealing portion includes at least one raised annular portion of said adapter body.

8. The threaded quick disconnect adapter of claim 1 further including a collar disposed between said first end and said second end of said adapter body.

9. The threaded quick disconnect adapter of claim 1 wherein said sealing member includes a least one raised annular portion of said adapter body.

10. A threaded quick disconnect adapter for connecting surgical probes to a valve device, said adapter comprising:
    an adapter body having a first end and a second end, said adapter body defining an inner passageway extending from said first end to said second end;
    a valve engaging portion disposed on said first end of said adapter body, said valve engaging portion having a threaded region for threadably engaging a probe fitting of the valve device;
    a threaded probe engaging portion disposed on said second end of said adapter body for engaging a probe base on one of said probes, said threaded probe engaging portion having a first outer diameter; and
    a sealing portion disposed on said second end of said adapter body, wherein said sealing portion has a second outer diameter smaller than said first outer diameter of said threaded probe engaging portion, said sealing portion including:
        at least one annular groove;
        at least one O-ring seated in said annular groove for sealing with said probe base of said probe; and
        at least one raised annular portion for contacting an inner surface region of said probe base to provide a tactile indication of engagement.

11. The threaded quick disconnect adapter of claim 10 wherein said threaded probe engaging portion includes a thread providing less than ¼ turn to fully engage with said probe base.

12. The threaded quick disconnect adapter of claim 10 wherein said threaded probe engaging portion includes a thread having a maximum of 2 threads per inch.

13. A surgical assembly comprising:
    at least one probe having a probe tip and a threaded probe base; and
    a threaded quick disconnect adapter for removably attaching said at least one probe to a valve device, said threaded quick disconnect adapter comprising:
        an adapter body having a first end and a second end, said adapter body defining an inner passageway extending from said first end to said second end;
        a valve engaging portion disposed on said first end of said adapter body for engaging a probe fitting of the valve device;
        a sealing portion disposed on said second end of said adapter body for slidably engaging said threaded probe base using a linear motion, wherein said sealing portion includes at least one annular sealing member raised above a surface of said second end of said adapter body to seal against an inner region of said probe base; and
        a threaded probe engaging portion disposed on said second end of said adapter body for threadably engaging said threaded probe base on said probe using a turning motion.

14. The surgical assembly of claim 13 further including a valve device having at least one probe fitting.

15. The surgical assembly of claim 13 wherein said valve engaging portion and said probe fitting are threaded.

16. The surgical assembly of claim 13 wherein said threaded probe engaging portion has an first outer diameter greater than a second outer diameter of said sealing portion.

17. The surgical assembly of claim 13 wherein said threaded probe engaging portion includes a thread providing less than ¼ turn to fully engage with said probe base.

18. The surgical assembly of claim 13 wherein said sealing portion includes at least one annular groove disposed around said second end of said adapter body, and wherein said at least one annular sealing member includes at least one O-ring seated within said at least one annular groove.

19. The surgical assembly of claim 18 wherein said sealing portion includes at least one raised annular portion of said adapter body.

20. The surgical assembly of claim 13 further including a collar disposed between said first end and said second end of said adapter body.

21. The surgical assembly of claim 13 wherein said sealing member includes at least one raised annular portion of said adapter body.

22. A surgical valve and probe assembly comprising:
   at least one probe having a probe tip and a probe base, said probe base having an internally threaded portion and an inner sealing portion;
   a valve device having at least one inlet and at least one threaded quick disconnect probe fitting for removably attaching said at least one probe to said valve device, said threaded quick disconnect probe fitting comprising:
      a probe fitting body;
      a threaded probe engaging portion disposed on said probe fitting body for engaging said probe base on said probe, said threaded probe engaging portion having a first outer diameter; and
      a sealing portion disposed on said probe fitting body for sealing with said probe base, said sealing portion having a second outer diameter smaller than said first outer diameter of said threaded probe engaging portion, said sealing portion including at least one annular sealing member raised above said second outer diameter of said sealing portion and below said first cuter diameter of said threaded probe engaging portion such that said internal threaded portion in said probe base passes over said sealing member and said inner sealing portion in said probe base engages said sealing member in a sealing engagement.

23. The surgical valve and probe assembly of claim 22 wherein said threaded probe engaging portion includes a thread providing less than ¼ turn to fully engage with said probe base.

24. A threaded quick disconnect adapter for connecting surgical probes to a valve device, said adapter comprising;
   an adapter body having a first end and a second end, said adapter body defining an inner passageway extending from said first end to said second end;
   a valve engaging portion disposed on said first end of said adapter body for engaging a probe fitting of the valve device;
   a threaded probe engaging portion disposed on said second end of said adapter body for engaging a probe base on one of said probes, said threaded probe engaging portion having a first outer diameter; and
   a sealing portion disposed on said second end of said adapter body, said sealing portion having a second outer diameter smaller than said first outer diameter of said threaded probe engaging portion, said sealing portion including at least one annular sealing member raised above said second outer diameter and below said first outer diameter for sealing against said probe base of said probe, wherein said threaded probe engaging portion is located between said sealing portion and said valve engaging portion.

* * * * *